United States Patent [19]
Palestrant

[11] Patent Number: 5,618,267
[45] Date of Patent: Apr. 8, 1997

[54] METHOD FOR ESTABLISHING COLLAPSIBLE INFUSION CONDUIT

[76] Inventor: Aubrey M. Palestrant, 6800 N. 47th St., Paradise Valley, Ariz. 85253

[21] Appl. No.: 539,991

[22] Filed: Oct. 6, 1995

Related U.S. Application Data

[62] Division of Ser. No. 282,036, Jul. 28, 1994, Pat. No. 5,472,418.

[51] Int. Cl.$^6$ .................................................. A61M 31/00
[52] U.S. Cl. .............................. 604/53; 604/43; 604/264; 604/280
[58] Field of Search ................................ 604/28, 43, 49, 604/50–3, 93, 96, 158, 160, 164, 167, 169, 170, 244, 245, 247, 256, 257, 266; 128/898

[56] References Cited

U.S. PATENT DOCUMENTS

| | | |
|---|---|---|
| 3,888,249 | 6/1975 | Spencer . |
| 4,141,364 | 2/1979 | Schultze . |
| 4,306,562 | 12/1981 | Osborne . |
| 4,406,656 | 9/1983 | Hattler et al. ............................ 604/280 |
| 4,445,897 | 5/1984 | Ekbladh et al. ......................... 604/280 |
| 4,469,483 | 9/1984 | Becker et al. ........................... 604/280 |
| 4,529,399 | 7/1985 | Groshong et al. ....................... 604/170 |
| 4,738,666 | 4/1988 | Fuqua ..................................... 604/280 |
| 5,045,075 | 9/1991 | Ersek ...................................... 604/264 |
| 5,106,368 | 4/1992 | Uldall et al. .............................. 604/43 |
| 5,176,659 | 1/1993 | Mancini .................................. 604/280 |
| 5,209,726 | 5/1993 | Goosen ................................... 604/280 |
| 5,256,150 | 10/1993 | Quiachon et al. ....................... 604/169 |
| 5,322,516 | 6/1994 | Brugger .................................. 604/264 |

OTHER PUBLICATIONS

"Gravity Drains/Penrose Drains", General Line Products, Davol, Inc. subsidiary of C.R. Bard, Inc., Cranston, Rhode Island, Jan., 1992.

*Primary Examiner*—V. Millin
*Assistant Examiner*—Bhisma Mehta
*Attorney, Agent, or Firm*—Cahill, Sutton & Thomas, P.L.C.

[57] ABSTRACT

An apparatus and method for establishing a collapsible infusion conduit in a blood vessel includes a catheter formed as a normally-flattened tube of flexible, collapsible plastic. When placed in a blood vessel, the catheter collapses to a flattened configuration for lying along the wall of the blood vessel to avoid obstruction to blood flow. During infusion, infusion fluid expands the catheter to a generally oval flow path. The catheter may be initially placed in the blood vessel by pre-loading the catheter over a guide wire and inserting the catheter and guide wire through an introducer sheath into the blood vessel. Infusion fluid is thereafter applied to the trailing end of the catheter to expand the catheter to facilitate withdrawal of the guide wire. Alternatively, the leading end of the catheter may initially be sealed, and placement into the blood vessel is achieved through an introducer sheath by inflating the catheter with pressurized fluid to temporarily render the catheter rigid and generally oval. The seal at the leading end of the catheter is thereafter opened, either by inserting a guide wire into the catheter to pierce the sealed end, or by increasing the inflation pressure to burst a weakened break line formed at the leading end of the catheter.

7 Claims, 3 Drawing Sheets

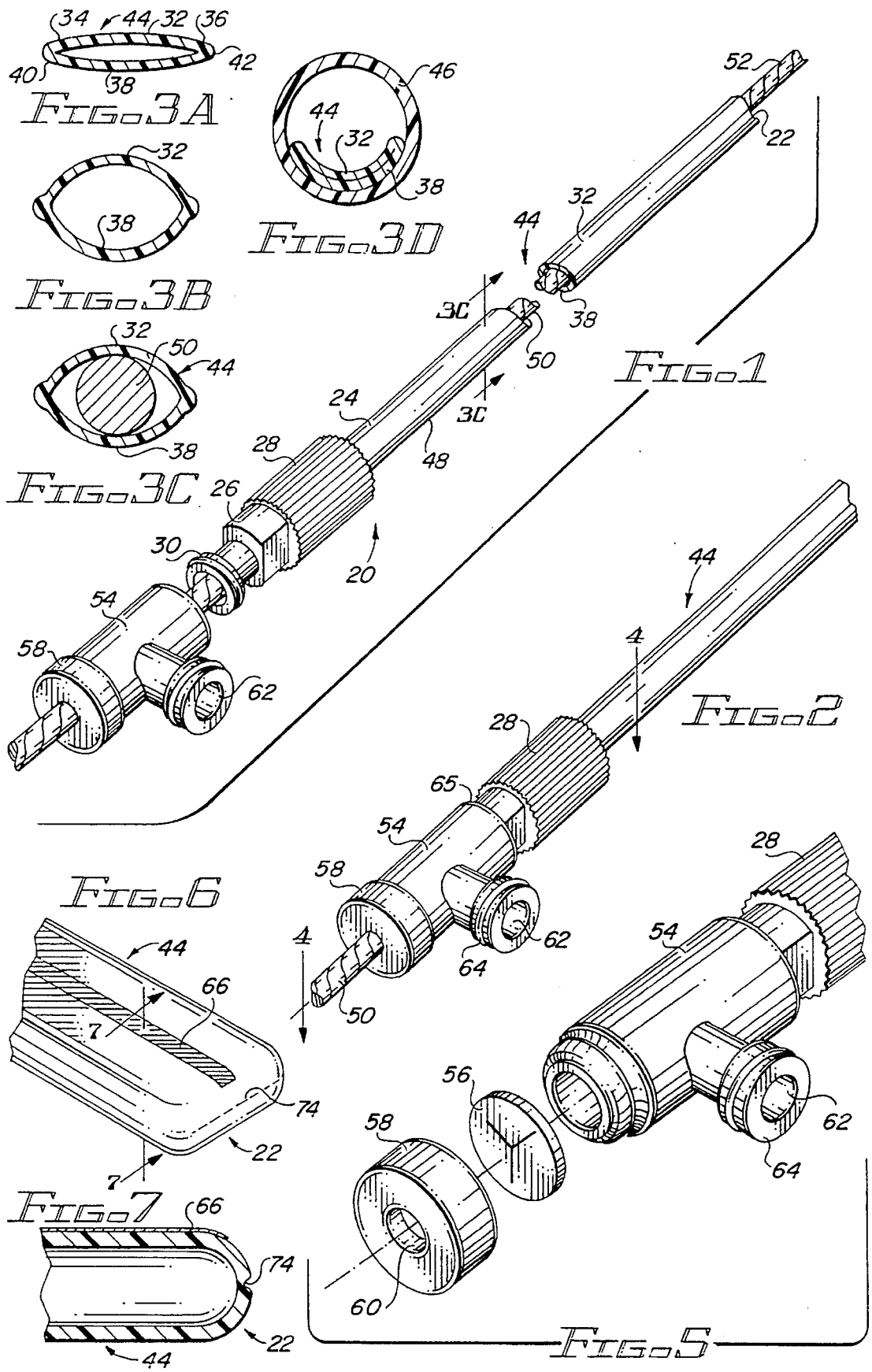

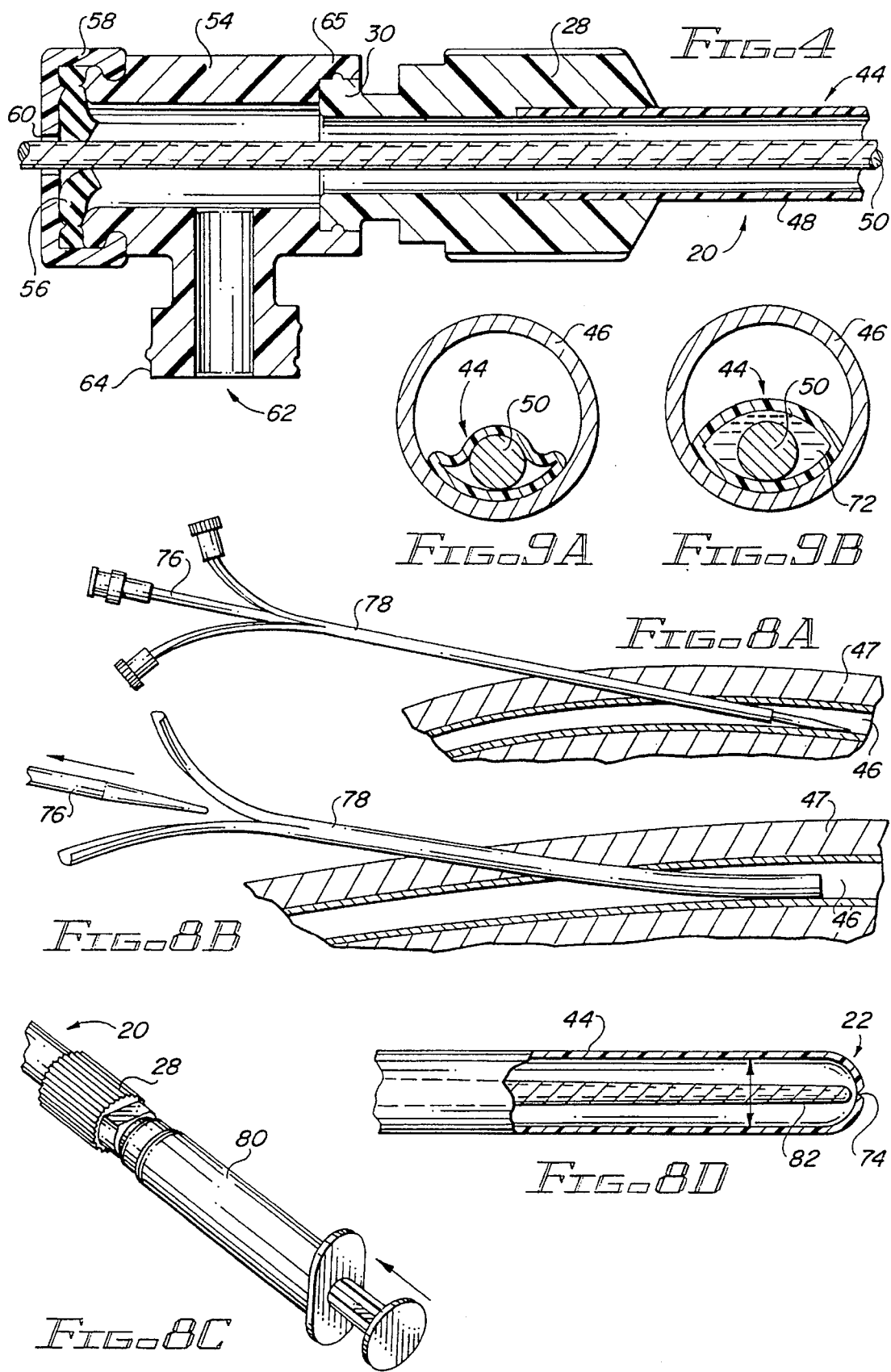

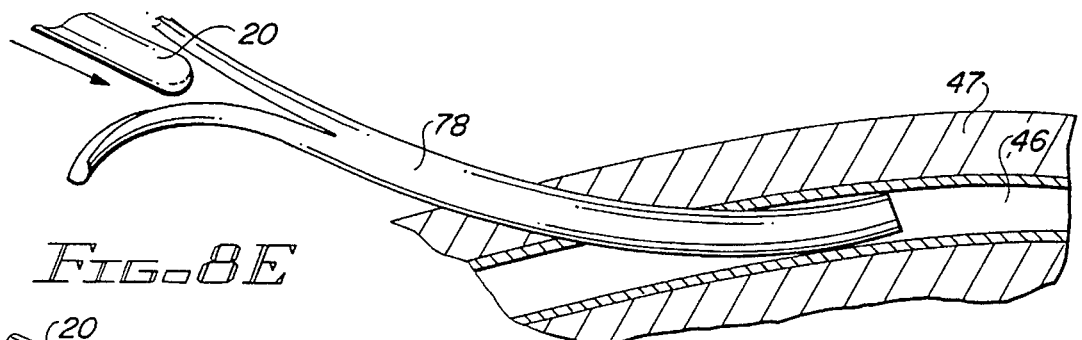
FIG._8E
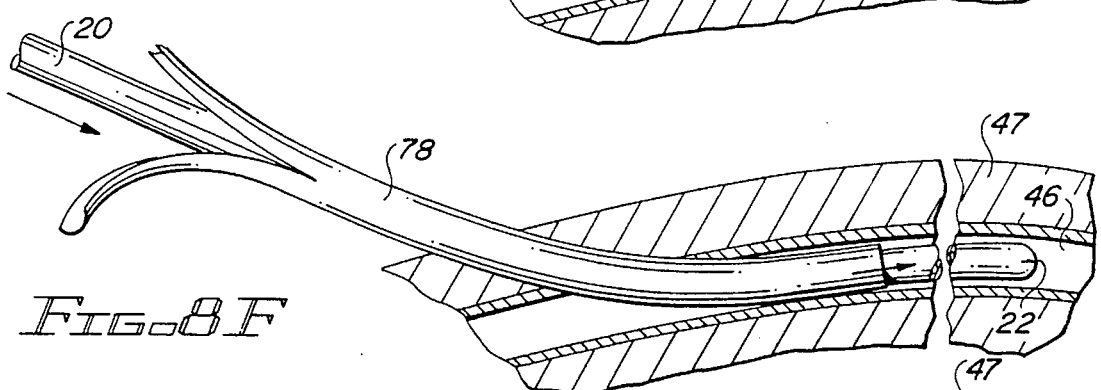
FIG._8F
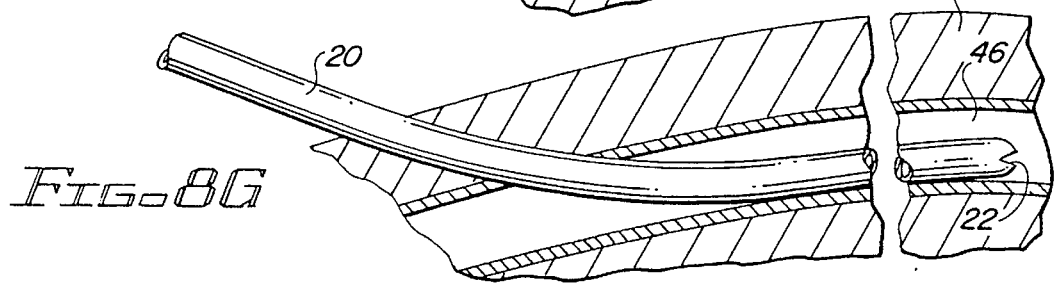
FIG._8G
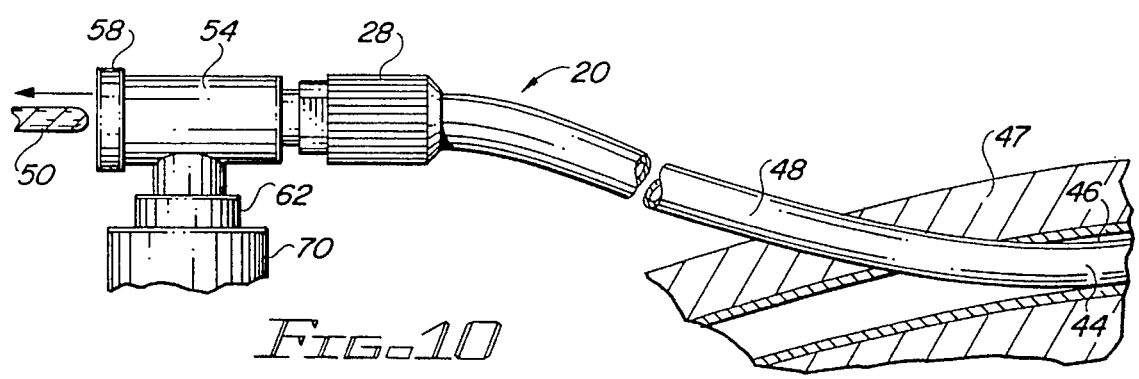
FIG._10
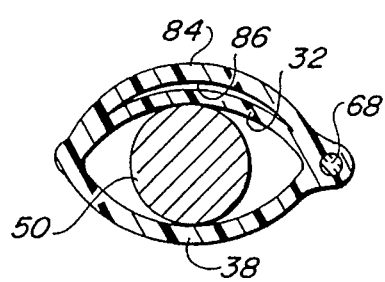
FIG._11
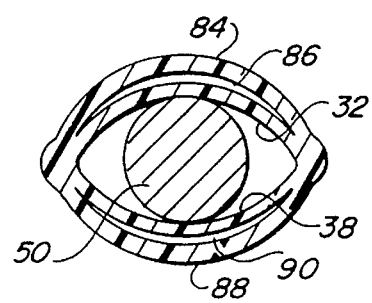
FIG._12

METHOD FOR ESTABLISHING COLLAPSIBLE INFUSION CONDUIT

This is a division of application Ser. No. 08/282,036, filed Jul. 28, 1994, now U.S. Pat. No. 5,472,418.

BACKGROUND OF THE INVENTION

1. Field of the Invention

The present invention relates generally to catheters inserted into the vascular system for extended periods of time, and more particularly, to a collapsible catheter for insertion into a blood vessel, and methods for placing such collapsible catheter into the blood vessel.

2. Description of the Related Art

Insertion of catheters into the vascular system of humans and animals is a commonly performed procedure. These catheters function as a conduit for infusion of fluids or drugs. When a catheter needs to be in place for greater than three or four days, it is common to place a so-called central line catheter, and to locate the leading tip of the catheter in one of the major veins at the top of the chest leading to the heart, such as the subclavian vein or the major veins of the mediastinum. In some instances, but less commonly, catheters are passed from the lower half of the body into the inferior vena cava. Central catheters are usually passed into the subclavian vein, jugular vein, or into an antecubital vein at the elbow. Such central catheters may have single or multiple lumens, and are typically made from a relatively rigid plastic material with a standard, round cross-section, both to facilitate placement of the catheter into the vein and to prevent the catheter lumens from collapsing within the vein. Generally speaking, these catheters are constructed in such a way that the lumen or lumens extending therethrough retain their cross-sectional configuration unless an external mechanical force compresses the catheter.

A complication of placing a central line catheter is the formation of clots on the wall of the catheter located in the vascular system. Blood clots form for several reasons. The presence of any object occupying space within a blood vessel causes turbulence and slowing of the blood flow through the vessel, and these factors induce the formation of clots. Generally, the greater the cross-sectional area of the catheter relative to the blood vessel, the greater the induced turbulence and slowing of the blood. In addition, the catheter is a foreign body, and the surface of the catheter in contact with blood acts as a nidus for clot formation. Once again, the greater the amount of surface area of the catheter or other foreign body in contact with the blood, the more likely that clots will form.

Such clots can break away and flow in the blood stream to the heart and lungs, causing severe complications. Furthermore, the formation of clots can often cause such veins to become irreversibly damaged and thrombose, preventing further blood flow through such veins. This may ultimately cause debilitating swelling of the limb being drained by these veins.

Apart from the risks of forming clots within the blood vessel, present central line catheters also suffer from susceptibility to clotting within the catheter itself. In this regard, blood enters the lumen of the catheter and forms a clot within the lumen, obstructing the passage of fluids through the catheter into the vein, and thereby rendering it unusable. While such clots may not be life threatening to the patient, blockage of the catheter can require removal and replacement of the catheter, a procedure which poses an inconvenience to both the patient and the attending physician, and adds to the cost of maintaining venous access.

U.S. Pat. No. 5,176,659 issued to Mancini discloses an expandable intravenous catheter which has a lesser diameter during insertion into a vein, and which is thereafter expanded following placement to a larger diameter. While such device simplifies insertion of the catheter, it still maintains a sizable obstruction within the vein with a significant exposed surface area, and it still permits blood to enter the lumen of the catheter in the absence of fluid flow.

U.S. Pat. No. 5,106,368 to Uldall et al. discloses a dual lumen catheter for vascular access. The distal portion of the catheter includes two tubular members attached to each other, only one of which is collapsible. The catheter is inserted into a blood vessel through a peel-away sheath, and over both a stiffening cannula and a guide wire. The collapsible lumen returns to its original circular shape once placed in the blood vessel. Thus, no reduction of the cross-sectional area, or surface area, of the catheter is achieved after the catheter is placed. In addition, blood can still enter both lumens of the catheter in the absence of fluid flow.

U.S. Pat. No. 4,406,656 issued to Hattler et al. discloses a multi-lumen catheter adapted to be inserted through the center of an insertion needle into the vein of a patient. The catheter disclosed by Hattler et al. includes two or more collapsible lumens formed around a flexible, but non-collapsible, central lumen. The collapsible lumens expand outwardly under the pressure of fluid flow and collapse to a smaller cross-sectional area in the absence of fluid flow. However, the central lumen of the Hattler et al. device is formed of materials which retain the shape of the central passageway whether or not fluids flow therethrough. Thus, even when the collapsible lumens are collapsed, the device disclosed by Hattler et al. still approximates the cross-sectional area of a conventional single lumen catheter. Indeed, Hattler et al. state that the central lumen of the disclosed multi-lumen catheter requires a certain degree of stiffness or rigidity to provide sufficient structural support so that the catheter can be handled as are conventional catheters. While the device disclosed by Hattler et al. somewhat reduces the cross-sectional area of a multi-lumen catheter, it does not reduce the cross-sectional area or surface area of the catheter below that of a conventional single lumen catheter, nor does it prevent blood from entering the central, non-collapsible lumen in the absence of fluid flow.

Accordingly, it is an object of the present invention to provide a central line catheter which reduces the likelihood of the formation of clots within the blood vessel into which the catheter is placed.

It is another object of the present invention to provide such a catheter which presents a minimal cross-section obstruction to the normal flow of blood within the blood vessel when the catheter is not being used for infusion, while providing a satisfactory flow path to infused fluids during infusion procedures.

It is still another object of the present invention to provide such a catheter which minimizes the surface area of the catheter exposed to the blood when infusion procedures are not being performed.

It is a further object of the present invention to provide such a catheter which minimizes the likelihood of blood entering the lumen of the catheter and forming a blockage therein.

A still further object of the-present invention is to provide a method for conveniently placing such a catheter within the desired blood vessel using commonly available vascular apparatus.

These and other objects of the present invention will become more apparent to those skilled in the art as the description of the present invention proceeds.

SUMMARY OF THE INVENTION

Briefly described, and in accordance with the preferred embodiments thereof, the present invention is a collapsible vascular infusion catheter apparatus for providing an infusion passage into a blood vessel while occupying minimal space, and presenting minimal surface area within the blood vessel, when infusion is not being conducted. The catheter of the present invention includes at least first and second elongated, generally flattened strips of flexible material; suitable flexible material include without limitation plastic sheets formed of polyethylene, polyethylene teraphthalate, and polyvinyl chloride. The respective sides of the first and second strips are joined with each other to form an elongated, normally-flattened tube having an inner lumen and having first and second opposing ends. The first, or trailing, end of the tube is adapted to receive fluid to be infused into a blood vessel of a patient, and the second, or leading, end of the tube provides an exit port through which fluid received at the first end of the tube can be introduced into a blood vessel of a patient.

The normally-flattened tube expands toward a generally oval shape, depending upon the rate of infusion, when fluid is infused into a blood vessel of a patient, thereby providing an open path for the infusion fluid. When the infusion procedure is terminated, the tube collapses back to a generally flattened configuration for lying adjacent a wall of the blood vessel. In this manner, the tube presents minimal cross-sectional obstruction to the flow of blood within the blood vessel, and also presents minimal surface area exposed to the blood flowing in the blood vessel. In addition, the tube acts like a valve by sealing the tip of the tube when the tube collapses to prevent blood from entering the lumen of the catheter.

The preferred embodiment of the above-described catheter includes a radiopaque marker to allow the catheter to be viewed by X-ray or fluoroscope to ensure that the catheter has been positioned within the selected blood vessel as desired. This radiopaque marker may take the form of a radiopaque stripe applied to one face of the tube, a radiopaque marker located at the leading end of the tube, or a radiopaque wire extending along one seam of the catheter.

Alternate embodiments of the present invention include similarly collapsible catheters having two or more lumens formed therein. For example, a second lumen may be provided by including a third elongated, generally flattened strip of the same flexible material extending generally along at least one of the first and second strips, and joining the respective sides of third strip with those of the first and/or second strips to form a second elongated, normally-flattened tube having a second lumen in parallel with the first lumen.

In order to facilitate handling of the first, or trailing, end of the catheter after placement, and to prevent unintended damage to the tube at the skin entry point, the first end of the tube may include a more rigid skin entry portion extending from the hub of the catheter to the entry point of the blood vessel.

Another aspect of the invention relates to the apparatus and method for placing the catheter within the patient's blood vessel. One such procedure uses a cylindrical guide wire initially extending through the lumen of the normally-flattened tube to rigidify the tube and to shape the tube into a generally oval shape for insertion into a blood vessel of the patient. The catheter is pre-loaded over the guide wire prior to insertion, with the tip portion of the guide wire extending through and beyond the exit port of the tube. An entry path is established through the patient's skin into a blood vessel, as by placing an introducer sheath using standard angiographic techniques. The guide wire and the leading end of the tube are inserted as a unit through the entry path and into the blood vessel. The catheter and guide wire are advanced together through the blood vessel to a desired location using fluoroscopic, ultrasonic, or X-ray guidance.

Following insertion in the manner described above, the introducer sheath is removed (assuming that one was used), while temporarily leaving both the guide wire and catheter in place. The guide wire is then removed from the tube while leaving the second, or leading, end of the tube within the blood vessel at the desired location and allowing the inserted portion of the tube to collapse against the wall of the blood vessel. To facilitate the release of the guide wire from the lumen of the tube, the present invention may include a mechanism for temporarily infusing fluid into the first, or trailing, end of the tube while the guide wire is present within the catheter for expanding the tube. The infused fluid expands the tube, freeing the tube from the guide wire, thereby allowing the guide wire to be more easily withdrawn by pulling the same from the first end of the tube.

An alternate procedure for placing the collapsible catheter of the present invention in a selected blood vessel involves the initial formation of a seal at the second, or leading, end of the tube for allowing the tube to be inflated by fluid under pressure. The seal initially formed at the second end of the tube is adapted to be broken for providing the exit port. After establishing an entry path through the patient's skin into the blood vessel, an introducer sheath is inserted through the entry path and into the blood vessel. The introducer sheath provides an entry passageway into a blood vessel into which the tube is to be placed. Next, a device for applying a fluid under pressure, such as a syringe, is releasably coupled to the first end of the normally-flattened tube to rigidify the tube and to temporarily form the tube into a more oval shape to facilitate passage of the tube through the introducer sheath for placement within the blood vessel. The leading end of the tube is then inserted into the introducer sheath and into the blood vessel while maintaining the fluid within the tube under pressure. Once the catheter has been advanced to the desired location using fluoroscopic, ultrasonic, or X-ray guidance, the introducer sheath is removed from the entry path while leaving the tube within the blood vessel.

Before the catheter placed in the above-described manner can be used, the seal initially formed at the second end of the tube must first be broken for allowing fluid within the tube to exit into the blood vessel. In one embodiment of the present invention, a seal-breaking apparatus is inserted into the tube after the syringe or other pressure application mechanism is removed. The seal-breaking apparatus is extended along the length of the tube to a point proximate the second end of the tube for opening the seal at the second end of the tube. Such a seal-breaking apparatus may include a simple guide wire which is inserted into the tube along the length of the tube to a point proximate the second end of the tube for piercing the second end of the tube.

In another embodiment of the present invention, the seal formed at the second end of the tube is broken remotely by further increasing the inflation pressure applied to the tube. In this embodiment, the seal initially formed at the second end of the tube includes a weakened break line that ruptures when fluid pressure within the tube exceeds a predetermined value. During placement of the catheter into the blood vessel through the introducer sheath, the fluid pressure is maintained below this predetermined value to avoid premature rupture of the seal. Once the catheter is properly placed, the fluid pressure is increased up to the predetermined burst value to rupture the seal along the weakened break line for providing the exit port.

BRIEF DESCRIPTION OF THE DRAWINGS

FIG. 1 is a perspective view of a collapsible venous infusion catheter in accordance with a first embodiment of the present invention.

FIG. 2 is a partial perspective view of the collapsible catheter shown in FIG. 1 with an attached guide wire diaphragm having a side-mounted infusion port.

FIG. 3A is a cross-sectional view of the collapsible catheter of FIG. 1 in its collapsed condition.

FIG. 3B is a cross-sectional view of the collapsible catheter shown in FIG. 1 in its expanded condition.

FIG. 3C is a cross-sectional view of the collapsible catheter shown in FIG. 1 taken through the plane designated by lines 3C in FIG. 1.

FIG. 3D is a cross-sectional view of the collapsible catheter collapsed against the surrounding wall of a blood vessel into which the catheter has been placed.

FIG. 4 is a cross-sectional view of the infusion end of the collapsible catheter, and related guide wire diaphragm/infusion port taken through the plane indicated by line 4 in FIG. 2.

FIG. 5 is an exploded perspective view of the guide wire diaphragm/infusion port shown in FIGS. 1 and 2.

FIG. 6 is a perspective view of the second, or leading, end of the collapsible catheter, and including a radiopaque stripe and a weakened break line.

FIG. 7 is a cross-sectional view of the forward tip of the collapsible catheter shown in FIG. 6 viewed through the plane designated by lines 7 within FIG. 6.

FIG. 8A is a partially sectioned view of a patient's vein lying below the skin, and illustrating the placement of a peal-away introducer sheath along the entry path into the vein.

FIG. 8B illustrates the introducer sheath within the patient's vein following removal of its accompanying dilator.

FIG. 8C is a perspective view of a syringe coupled to the trailing end of the collapsible catheter.

FIG. 8D is a sectional view of the tip of the collapsible catheter and showing the tip of a guide wire inserted into the collapsible catheter and about to pierce the sealed leading end thereof.

FIG. 8E illustrates the entry of the second, or leading, end of the collapsible catheter into the introducer sheath.

FIG. 8F illustrates the inflated collapsible catheter following insertion through the introducer sheath.

FIG. 8G illustrates the collapsible catheter following removal of the sheath, and immediately following bursting of the initially sealed tip of the catheter.

FIG. 9A illustrates a cross-sectional view of the collapsible catheter and supporting guide wire, as shown in FIG. 1, immediately following placement of the catheter into a vein.

FIG. 9B is a cross-sectional view of the collapsible catheter and supporting guide wire after infusing fluid into the catheter for allowing the guide wire to be withdrawn.

FIG. 10 is a side view showing a portion of syringe coupled to the side-mounted infusion port of the guide wire diaphragm device for infusing fluid into the collapsible catheter to free the guide wire from the walls of the catheter.

FIG. 11 is a cross-sectional view of a dual lumen collapsible catheter constructed in accordance with the teachings of the present invention, supported by a stiffening guide wire, and including a radiopaque marking wire.

FIG. 12 is a triple lumen collapsible catheter constructed in accordance with the teachings of the present invention and including a supporting insertion guide wire.

DETAILED DESCRIPTION OF THE PREFERRED EMBODIMENTS

FIG. 1 illustrates a first embodiment of a fully-collapsible venous infusion catheter apparatus for providing an infusion passage into a vein in accordance with the teachings of the present invention. While the preferred embodiment of the present invention described herein is placed in a vein, the present invention is not intended to be limited to use with veins, but should be understood to extend to any blood vessel. The collapsible catheter is designated generally by reference numeral 20 within FIG. 1, and includes a leading open end 22 and an opposing trailing end 24. Leading end 22 provides an exit port through which fluid received at trailing end 24 can be introduced into a vein of a patient. Trailing end 24 terminates in a conventional rigid plastic body 26 having a knurled collar or hub 28 to facilitate handling. A conventional luer lock connector fitting 30 is provided at the end of body 26 for connection to syringes, infusion lines and the like for receiving fluid to be passed through catheter 20 to exit port 22.

Referring to FIG. 3A and 3B, the collapsible portion of catheter 20 includes a first elongated, generally flattened strip 32 of flexible material having first and second opposing sides 34 and 36. First strip 32 extends the length of catheter 20 from trailing end 24 to leading end 22. The collapsible portion of catheter 20 also includes a second elongated, generally flattened strip 38 of flexible material having first and second opposing sides 40 and 42, and like first strip 32, extends the length of catheter 20 from trailing end 24 to leading end 22. First side 40 of second strip 38 is joined with the first side 34 of first strip 32; likewise, second side 42 of second strip 38 is joined with the second side 36 of first strip 32 to form an elongated, normally-flattened, collapsible tube 44 having opposing ends 22 and 24.

Tube 44 is shown in its collapsed configuration in FIG. 3A prior to placement in a vein. Within FIG. 3D, tube 44 is shown collapsed against the inner wall of vein 46 following placement in the vein, and in the absence of fluid flow therethrough. This is the configuration which the inventor anticipates tube 44 will assume in the vein in the absence of the flow of infusion fluid therethrough. In this collapsed configuration, tube 44 occupies minimal space within the vein when infusion is not being conducted, and therefore causes minimal turbulence and slowing of blood flow within vein 46. In addition, because almost one-half of the surface of tube 44 lies adjacent the wall of vein 46 when in the collapsed condition shown in FIG. 3D, the amount of surface area of tube 44 exposed to blood flow within vein 46 is minimized. All of these features lessen the likelihood of blood clot formation within vein 46. In addition, since exit port 22 of tube 44 also assumes the collapsed configuration shown in FIG. 3D in the absence of fluid flow, blood is prevented from entering the lumen of tube 44 between infusion procedures, thereby lessening the possibility for clots to form within the lumen, and the resulting blockage of infusion fluid. Thus, the collapsible leading end of tube 44 functions like a one-way flap valve to permit infusion fluid to escape therefrom and to prevent blood from entering therein.

As shown in FIGS. 3B and 9B, tube 44 can be expanded by infusing fluid through tube 44. The normally-flattened tube 44 expands to a generally oval shape when fluid is infused into a vein of a patient, thereby providing a sizable cross-sectional path for fluid to be passed into the vein. When infusion is terminated, tube 44 collapses back to the generally flattened configuration shown in FIG. 3D for lying adjacent the wall of the vein.

While strips 32 and 38 have been described as discrete strips joined along their respective sides, it should be understood that strips 32 and 38 may be integrally formed with each other, and that the described joinder of the side edges of such strips may, in fact, constitute the formation of pleats or folds in what is otherwise a single, smooth continuous surface. Suitable materials for forming strips 32 and 38 include strong but flexible plastic films, including those made of polyethylene, polyethylene teraphthalate, and polyvinyl chloride. In the preferred embodiment of the present invention, these plastic films are inelastic, although plastic films which exhibit elasticity might also be used.

Referring back to FIG. 1, tube 44 includes a skin entry portion 48 extending adjacent trailing end 24 of tube 44, and adjacent hub 28; this skin entry portion ultimately extends through the skin of the patient at the point of entry following placement of the catheter. If desired, this skin entry portion 48 of tube 44 may be made relatively rigid for a length of approximately eight to ten centimeters, as measured from hub 28, to facilitate handling of the catheter by medical personnel following placement, and to prevent damage to catheter 20 from long term manipulation.

As noted above, it is desired to make the majority of tube 44 that lies within the vein fully collapsible. However, a catheter that has no rigidity is almost impossible to insert into a vein as compared with a catheter which has rigidity. Accordingly, another aspect of the present invention relates to the apparatus and method used to place such a fully collapsible catheter within a vein. One such apparatus and method is shown in FIGS. 1 and 3C, wherein catheter 20 is pre-loaded onto a cylindrical guide wire 50 that initially extends through normally-flattened tube 44 to rigidify tube 44 and to temporarily shape it into a generally oval shape for insertion into the vein of a patient. As used in this specification and within the claims which follow, the term generally-oval should be understood to include cylindrical shapes. FIGS. 3C, 9A, and 9B illustrate the space within tube 44 surrounding guide wire 50 as being relatively large for clarity and to simplify the drawings. In practice, the inventor anticipates that guide wire 50 would closely approximate the internal "diameter" of tube 44, thereby providing a relatively close fit between tube 44 and guide wire 50 to avoid bunching of tube 44 along guide wire 50 during insertion. Guide wire 50 has a tip portion 52 which extends through and beyond exit port 22 of tube 44 during insertion.

Prior to insertion of catheter 20 and guide wire 50 into the vein of the patient, a guide wire diaphragm/side infusion port device 54 is slid over the trailing end of guide wire 50, as shown in FIG. 1. As shown best in FIGS. 4 and 5, device 54 includes a split seal diaphragm 56 secured thereto by a threaded cap 58 having a central bore 60 formed therein. Guide wire 50 extends through bore 60 and is wipingly engaged by split seal diaphragm 56 to prevent the loss of blood or infused fluid around guide wire 50. Device 54 also includes a side port 62 which is preferably provided with a luer lock connector fitting 64 for receiving a syringe or other source of infusion fluid. As shown in FIGS. 2 and 4, device 54 also includes a luer lock fitting 65 which is engaged with mating luer lock fitting 30 of catheter 20 to form a fluid tight seal therebetween.

Next, an entry path is established through the skin. Such an entry path may be established, by way of example, using the Seldinger technique or modified Seldinger technique, both of which are well known to those skilled in the art. For example, using the modified Seldinger technique, an introducer sheath is inserted through the skin into the vein, providing a convenient passage for inserting the guide wire 50 and catheter 20, as a unit, into the vein. Proper placement of the leading end 22 of the catheter can be confirmed using X-rays, fluoroscopy, or ultrasound provided that a radiopaque marker stripe 66, like that shown in FIGS. 6 and 7, is formed upon and along one of flattened strips 32 or 38 of tube 44. Alternatively, a radiopaque wire 68 can be incorporated within a seam or pleat of tube 44 for extending along the tube, as shown in FIG. 11.

Once proper placement of the catheter tip is confirmed, guide wire 50 is removed. However, as shown in FIGS. 3C and 9A, guide wire 50 closely approximates the internal diameter of tube 44, and excessive friction between guide wire 50 and tube 44 could dislodge tube 44 from its desired position within the vein and/or cause kinks in catheter 20. Accordingly, prior to removal of guide wire 50, a syringe 70 or other mechanism for injecting a fluid is coupled to side port 62 of diaphragm device 54, as shown in FIG. 10, for injecting fluid into the lumen of tube 44. As indicated in FIG. 9B, the injected fluid 72 further expands tube 44 and moves the internal walls thereof away from guide wire 50 while additionally lubricating guide wire 50, thus allowing guide wire 50 to be withdrawn from catheter 20 without dislodging catheter 20 within the vein or creating kinks therein. Upon removal of guide wire 50, device 54 is removed from luer lock connector fitting 30 of catheter 20. Tube 44 then collapses against the wall of the vein, as shown in FIG. 3D, until an infusion procedure is initiated.

A second method of rigidifying the catheter for insertion avoids the need for a guide wire and instead uses a pressurized fluid to inflate tube 44 for purposes of insertion. This second method requires that the leading end 22 of catheter 20 is initially sealed, as shown in FIGS. 6 and 7, rather than being open as described with respect to FIG. 1. As shown in FIGS. 6 and 7, leading end 22 of tube 44 is initially sealed, but the seal formed at the second end of tube 44 preferably includes a weakened break line 74 which is adapted to be broken for providing an exit port. As described in greater detail below, this seal is later broken either locally or remotely after the catheter is properly placed.

Prior to placement of catheter 20 using the pressurized fluid method, an introducer sheath is inserted into the vein, in the manner shown in FIG. 8A. The introducer sheath includes a stiffening dilator 76 and a pull-apart sheath 78. The introducer sheath assembly is itself guided into vein 46 over a guide wire (not shown). As indicated in FIG. 8B, the rigid dilator 76 is then removed, leaving the pull-apart sheath extending through the skin 47 and into vein 46, thereby providing an entry passageway into a vein into which tube 44 is to be placed.

The next step is to pressurize tube 44 with fluid to rigidify tube 44 and make it more oval. As indicated in FIG. 8C, an angiographic syringe 80 filled with contrast dye is releasably secured to luer lock fitting 30 of catheter 20, and the plunger of syringe 80 is depressed sufficiently to inflate tube 44 with contrast dye fluid. The materials suggested above for use in forming tube 44 are easily capable of withstanding a pressure of 5 Atmospheres without bursting, and such pressure is adequate to temporarily rigidify tube 44 for placement within the vein. While not illustrated, syringes which include pressure gauges are available and well known to those physicians practicing in the art. As indicated in FIGS. 8E and 8F, tube 44 of catheter 20 is then inserted into sheath 78 and advanced therethrough into vein 46 until sealed end 22 is positioned at a desired location within the vein, while maintaining pressure on the fluid within the tube. The presence of the contrast dye within tube 44, and the radiopaque markings on the tube, allows the catheter to be visible in X-rays or on a fluoroscope.

After properly positioning catheter 20, pull-apart sheath 78 is withdrawn from the entry path while leaving tube 44 within the vein. FIG. 8F shows catheter 20 within vein 46 following removal of sheath 78 but before pressure has been released from tube 44. The final step is to break the seal at the seal at the leading end 22 of tube 44 for allowing infusion fluid within the tube to exit into the vein. Two preferred methods of breaking the seal will now be described.

In the first seal breaking method, syringe 80 is removed from luer lock connector 30 of catheter 20, and a seal-breaking apparatus is inserted into tube 44 along the length of the tube to a point proximate leading end 22 of the tube for opening the seal therein. For example, as shown in FIG. 8D, the so-called seal-breaking apparatus consists of a guide wire 82 inserted into tube 44 along the length of the tube to a point proximate leading end 22; the leading tip portion of guide wire 82 is advanced into the sealed end of tube 44 for piercing the sealed end of the tube to create the exit port.

The second method for breaking the seal at the leading end of tube 44, after the tube is properly positioned within the vein, involves raising the fluid pressure within tube 44 beyond the burst strength of the weakened break line at the second end of the tube. As mentioned above, syringe 80 (see FIG. 8C) normally applies no more than 5 Atmospheres of pressure to the contrast fluid dye in tube 44 during insertion of catheter 20 to avoid premature rupture of the seal. However, syringe 80 is capable of applying at least 10 Atmospheres of pressure to the contrast dye fluid injected into tube 44. This higher pressure is adequate to rupture the seal along the weakened break line 74 at leading end 22 of tube 44 for providing the exit port. Confirmation of the successful rupture of the seal using this method can be confirmed using a fluoroscope by observing a puff of contrast dye emitted from the tip of the catheter.

While the embodiments of the invention described thus far provide a catheter having only a single lumen, a fully collapsible multi-lumen catheter may also be constructed in accordance with the teachings of the present invention. Referring to FIG. 11, a third elongated, generally flattened strip 84 of the same flexible material as strips 32 and 38 can be secured along its side edges with the respective side edges of first strip 32 to form a second elongated, normally-flattened tube in parallel with tube 44; the collapsed lumen of such second tube is designated in FIG. 11 by reference numeral 86. The original lumen of the first normally-flattened tube is pre-loaded upon guide wire 50, as shown in FIG. 11, prior to insertion into the vein. The third strip 84 may, if desired, be made of the same length as strips 32 and 38 to provide a second lumen 86 having an exit port at its leading end disposed at approximately the same point in the vein as the exit port of the first lumen. Alternatively, third strip 84 may be made shorter in length than strips 32 and 38 to create a shorter second lumen 86 having an exit port that is longitudinally displaced from the exit port of the first lumen. Each of the two tubes may be provided with its own catheter hub (not shown) at the trailing end of such tubes in order to allow for separate control over the fluids infused therethrough.

Likewise, in FIG. 12, a fourth elongated, generally flattened strip 88 of the same flexible material as strips 32, 38, and 84 can be secured along its side edges with the respective side edges of second strip 38 to form a third elongated, normally-flattened tube in parallel with tube 44; the collapsed lumen of such third tube is designated in FIG. 12 by reference numeral 90. The above-described insertion methods for catheter 20 apply equally well to the double and triple lumen catheters shown in FIGS. 11 and 12, respectively.

Those skilled in the art will now appreciate that an improved, fully collapsible venous infusion catheter has been described which presents minimal obstruction to blood flow within a vein, which presents minimal surface area in contact with blood flowing in the vein, and which prevents blood from entering the infusion lumen between infusion cycles, yet which expands to provide a relatively large infusion path during infusion procedures. While the present invention has been described with respect to several preferred embodiments thereof, such description is for illustrative purposes only, and is not to be construed as limiting the scope of the invention. Various modifications and changes may be made to the described embodiments by those skilled in the art without departing from the true spirit and scope of the invention as defined by the appended claims.

I claim:

1. A method for establishing an infusion conduit into a blood vessel and for allowing said conduit to collapse against the walls of the blood vessel when the conduit is not being used for infusion, said method comprising the steps of:

a. providing a normally-flattened tube of flexible material, the tube having a trailing end to receive fluid to be infused into a blood vessel of a patient, and having a leading end forming an exit port through which fluid received at the trailing end of said tube can be introduced into a blood vessel of a patient;

b. loading the normally-flattened tube over a guide wire to rigidify the tube and to temporarily form the tube into a more oval shape;

c. establishing an entry path through a patient's skin into a blood vessel;

d. inserting the guide wire and leading end of the tube as a unit through the entry path and into the blood vessel;

e. removing the guide wire from the tube while leaving the leading end of the tube within the blood vessel for allowing an inserted portion of the tube to collapse against the wall of the blood vessel; and f. selectively applying an infusion fluid to the trailing end of the tube, the applied infusion fluid expanding the tube to a generally oval shape within the blood vessel during infusion, the tube collapsing to a generally flattened configuration against the wall of the blood vessel when the infusion fluid is not being applied to the trailing end of the tube.

2. The method recited by claim 1 wherein the step of establishing the entry path into the blood vessel includes the step of placing an introducer sheath through the patient's skin and into the blood vessel.

3. The method recited by claim 1 wherein the step of removing the guide wire from the tube includes the steps of temporarily infusing fluid into the trailing end of the tube to expand the tube for freeing the tube from the guide wire, and then pulling the guide wire from the trailing end of the tube while the tube is expanded by the infusion fluid.

4. A method for establishing an infusion conduit into a blood vessel and for allowing said conduit to collapse against the walls of the blood vessel when the conduit is not being used for infusion, said method comprising the steps of:

- a. providing a normally-flattened tube of flexible material, the tube having a trailing end to receive fluid to be infused into a blood vessel of a patient, and having a leading end forming an exit port through which fluid received at the trailing end of said tube can be introduced into a blood vessel of a patient, the leading end of the tube initially being sealed;
- b. establishing an entry path through a patient's skin into a blood vessel;
- c. inserting an introducer sheath through the entry path and into the blood vessel;
- d. applying a pressurized fluid to the trailing end of the normally-flattened tube to rigidify the tube and to temporarily form the tube into a more oval shape;
- e. inserting the leading end of the tube into the introducer sheath and into the blood vessel while maintaining pressure on the fluid within the tube;
- f. withdrawing the introducer sheath from the entry path while leaving the tube within the blood vessel;
- g. breaking the seal at the leading end of the tube for allowing fluid within the tube to exit into the blood vessel; and
- h. selectively applying an infusion fluid to the trailing end of the tube, the applied infusion fluid expanding the tube to a generally oval shape within the blood vessel during infusion, the tube collapsing to a generally flattened configuration against the wall of the blood vessel when the infusion fluid is not being applied to the trailing end of the tube.

5. The method recited by claim 4 wherein the step of breaking the seal at the leading end of the tube includes the step of inserting a seal-breaking apparatus into the tube along the length of the tube to a point proximate the leading end of the tube for opening the seal at the leading end of the tube.

6. The method recited by claim 5 wherein the step of inserting the seal-breaking apparatus consists of inserting a guide wire into the tube along the length of the tube to a point proximate the leading end of the tube for piercing the leading end of the tube.

7. The method recited by claim 4 including the step of forming a weakened break line at the leading end of the tube, and wherein the step of breaking the seal at the leading end of the tube includes the step of increasing the pressure upon the pressurized fluid applied to the trailing end of the tube after the tube is properly positioned within the blood vessel for opening the seal along the weakened break line at the leading end of the tube.

* * * * *